United States Patent [19]
Huebner

[11] Patent Number: 5,556,399
[45] Date of Patent: Sep. 17, 1996

[54] BONE-HARVESTING DRILL APPARATUS AND METHOD FOR ITS USE

[76] Inventor: Randall J. Huebner, 18560 SW. Hart Rd., Aloha, Oreg. 97005

[21] Appl. No.: 389,115

[22] Filed: Feb. 14, 1995

[51] Int. Cl.$^6$ .......................... A61B 17/32; A61B 17/56; A61B 17/16
[52] U.S. Cl. .................. 606/80; 606/79; 606/170; 408/207
[58] Field of Search .................. 606/80, 81, 79, 606/170, 171, 180; 408/207, 227

[56] References Cited

U.S. PATENT DOCUMENTS

| | | | |
|---|---|---|---|
| 14,454 | 3/1856 | Hitchcock et al. | 408/207 |
| 77,819 | 5/1868 | Krebs. | |
| 469,057 | 2/1892 | Chesnut. | |
| 550,190 | 11/1895 | Myers. | |
| 1,493,240 | 5/1924 | Bohn. | |
| 1,807,126 | 5/1931 | Morrill et al.. | |
| 2,710,000 | 6/1955 | Cromer et al. | 606/180 |
| 3,112,743 | 12/1963 | Cochran et al.. | |

*Primary Examiner*—Michael Powell Buiz
*Assistant Examiner*—Scott B. Markow
*Attorney, Agent, or Firm*—Kolisch, Hartwell, Dickinson, McCormack & Heuser

[57] ABSTRACT

A coring drill used to harvest bone from a donor area of the human body is described. The drill bit in its preferred embodiment is formed with a cylindrical, hollow shaft and a half-conical tip or cutting head. The cutting head is provided with a sharpened edge which meets at an apex with a non-sharpened edge, forming an obtuse angle of approximately 120°. The sharpened edge is configured to cut into bone when the drill bit is rotated in a clockwise direction, with the apex directed against a section of bone, the cutting edge sheers off fragments of bone which are then drawn upwardly through the hollow shank of the drill bit. As the drill bit is forced downwardly, continuous cutting action occurs and the morselized bone can then be removed, as by use of the described hand tool, from the shank and used to build-up bone in other areas to which it is transplanted. The drill bit in its preferred embodiment fittingly mates on the distal end a fitting that renders the invented drill bit physically compatible with a conventional chuck. The bit includes a pair of diametrically opposed, oppositely inclined recesses that cooperate with a crossbar member within a bit-receiving bore of the fitting. When the aligned drill bit is pressed into the fitting, the crossbar member cams along the inclined recesses causing the bit to rotate relative to the fitting. The resulting frictional engagement between the recesses and the crossbar member, along with a detent assembly between the bit and the fitting, securely lock the bit onto the distal end of the fitting, yet render removal possible by the use of a removal tool that is also described.

19 Claims, 2 Drawing Sheets

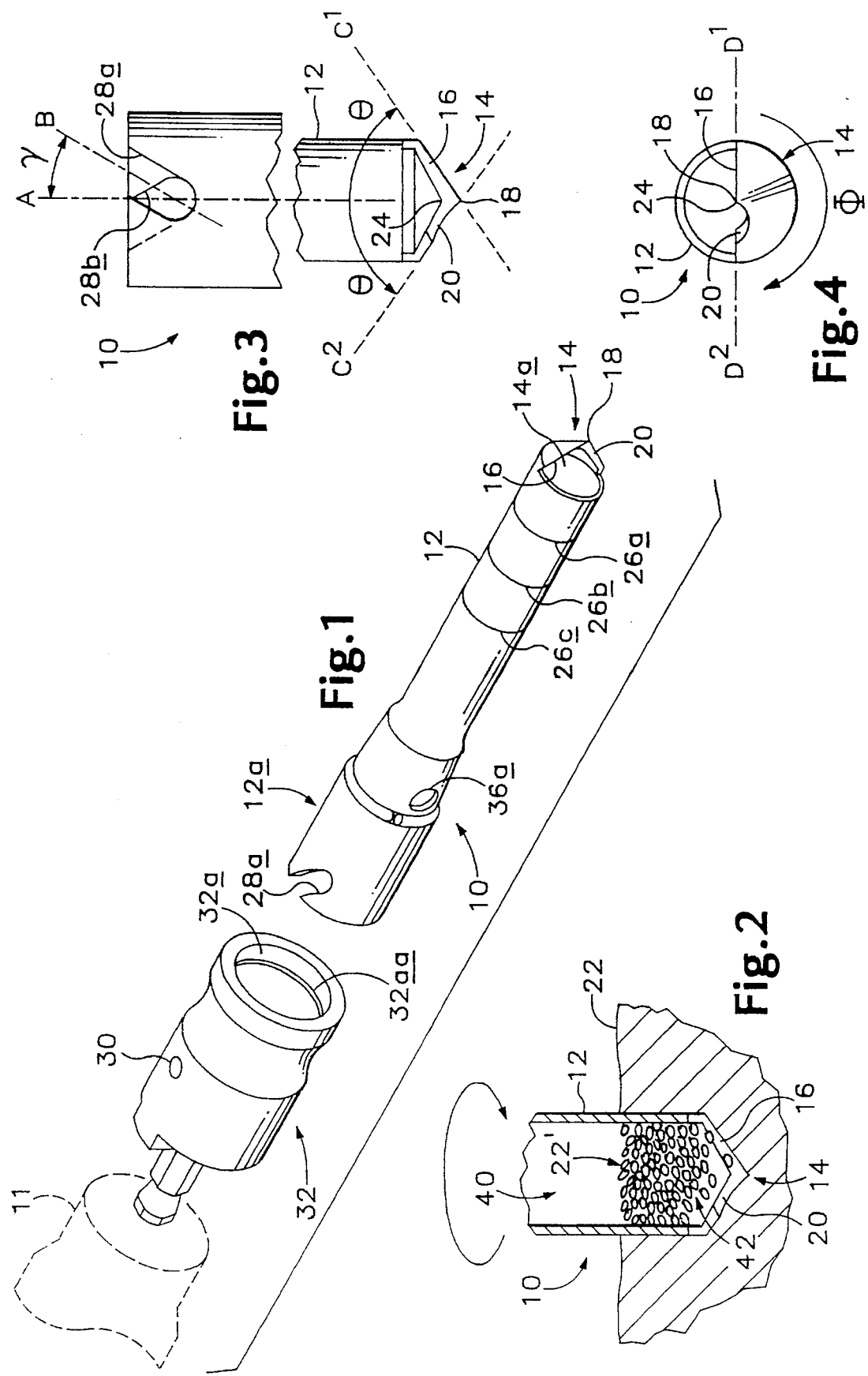

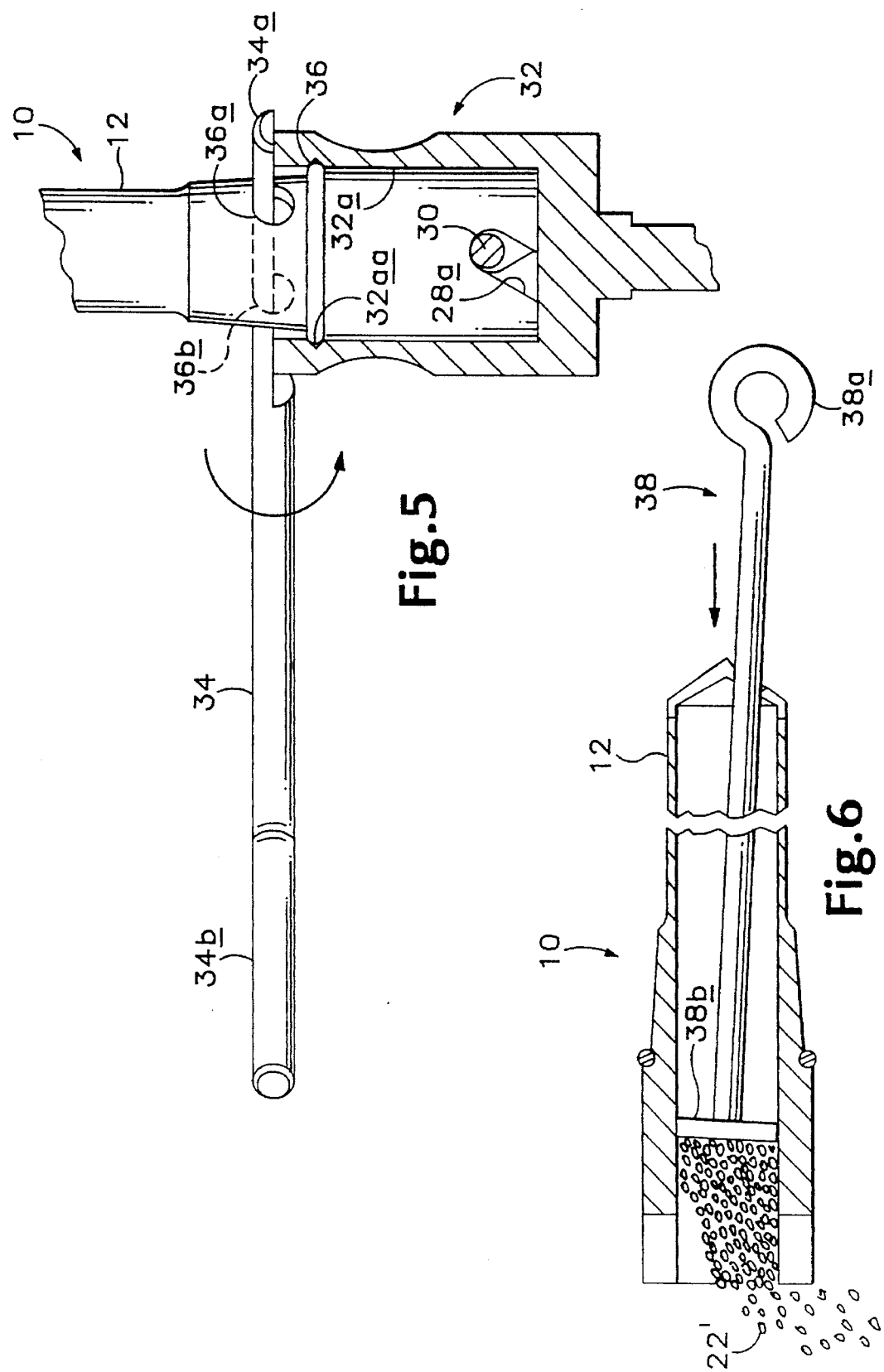

BONE-HARVESTING DRILL APPARATUS AND METHOD FOR ITS USE

BACKGROUND

The present invention relates generally to harvesting bone. More specifically, it concerns a bone-harvesting method and a to-be-used-therewith hollow, generally cylindrical coring drill bit and cooperative fitting assembly wherein the drill bit includes a locking end and cutting end having a cutting edge and an adjacent opening, the drill bit providing for the morselized removal of bone from a donor site and its collection within the drill bit's hollow shank region for transplantation at a donee site.

Bone is harvested for transplantation or grafting generally by one of two methods: it is removed in the form of a plug or it is removed in particulate form. In accordance with the latter, bone harvesting is performed by using a drill which bores and chips its way into the bone for the purpose of removing part of it in a granulated or morselized form, which is then transplanted or grafted onto another bony area. The granulated or morselized form is best for transplanting because it can be packed into another area where bone has been eroded, for example in an arthritic joint or other area in which bone has been diminished. Typical ways that bone may be removed or harvested is by using an osteotome which is a fine-bladed chisel used to remove a wedge of bone for transfer to another area. The second way is by use of a chipping-type drill, as in the present invention.

U.S. Pat. No. 3,112,743, entitled METHOD FOR TREATMENT OF BONE FRACTURES, discloses an axially and radially ported chipping-type bit used to drill holes in bones in preparation for injection of polyurethane foam into the medullary canal for treatment of broken or fractured bones. The disclosed bit has a tapered tip of a half-conical shape exposing symmetric clockwise- and counterclockwise-rotational cutting edges. The tapered tip also has an end opening defined on the tapered surface to guide pulverized bone fragments away from a connected hollow tube through which the polyurethane is to be injected. The end opening within the bit also allows the injected polyurethane to spread radially as well as axially through the medullary canal. Because the drill bit is meant for drilling holes in bone and not for collection of bone fragments for harvesting, it is structured to allow polyurethane to be injected out of the bit rather than letting harvested fragments in. Thus, its cutting head is sharply pointed at an acute angle, thereby permitting relatively shallow-angle drilling and injecting, i.e. drilling and injecting with the long axis of the drill bit at an acute angle to the plane of the bone's surface.

SUMMARY OF INVENTION

Essentially, the invention concerns a novel type of coring drill which is used to harvest bone from a donor area of the human body, typically the iliac crest of the hip bone, for transplantation to another area. Specifically, the invented drill bit in its preferred embodiment is formed with a cylindrical, hollow shaft and a semi-circumferentially extending conical tip or cutting head. The cutting head is provided with a sharpened or beveled cutting edge which meets at an apex with a non-cutting edge, forming a preferably obtuse angle therebetween of preferably approximately 120°. The sharpened edge is configured to cut into bone when the drill bit is rotated in a clockwise direction, with the pointed apex directed against a section of bone, the cutting edge sheers off fragments of bone which are deflected by the spinning semicircumferentially extending conical inner surface of the tip of the drill bit and then are drawn upwardly into the hollow shaft region of the drill bit. As the drill bit is forced downwardly, continuous cutting action occurs and the morselized bone can then be removed from the tube and used to build-up bone in other areas to which it is removed.

The drill bit in its preferred embodiment includes on its proximal end a pair of diametrically opposed and oppositely spirally extending or inclined recesses each having a structure which renders the drill bit easily and securely inserted within an invented fitting that renders the drill bit compatible with a Trinkle™, Zimmer™ or other desired industry-standard chuck. The cylindrical bore in the fitting that receives the drill bit is equipped with a crossbar member for mating engagement with the pair of recesses of the drill bit. The drill bit shank also is provided with a spring washer that extends around a circumferentially extending channel formed in the bit's shank near its proximal end. The fitting is equipped with a corresponding circumferential detent within the bore.

When the drill bit is pressed into the fitting's bore with the recesses aligned with opposite ends of the crossbar member, a slight pressure is all that is required securely to lock the bit within the fitting, as the crossbar member itself cams along the inclined recesses causing the bit to rotate relative to the fitting. The frictional engagement of the recesses with the crossbar member, as well as a press fit between the spring washer and the detent, securely holds the bit within the fitting. Thus, the bit cannot inadvertently escape the fitting. The bit may be removed by prying the bit from the fitting with a removal tool that is extended through a hole bored transversely through the bit's shank near its proximal end.

These and other objects and advantages of the invention will be more fully understood by reference to the accompanying drawings and the detailed description to follow.

BRIEF DESCRIPTION OF THE DRAWINGS

FIG. 1 is an isometric, exploded view of the invented drill bit showing its conical sectional tip end, hollow shaft region and locking end region, as well as a fragmentary view of the fitting which receives it.

FIG. 2 is a fragmentary view of the bit of FIG. 1 harvesting a donor bone region shown in cross section.

FIG. 3 is a fragmentary front elevation of the invented bit, and schematically illustrates certain of the important angular relationships of the tip's conical configuration and of the locking end region's and fitting's novel structures.

FIG. 4 is an end view of the invented bit that illustrates another of the important angular relationships of the tip's conical configuration.

FIG. 5 illustrates removal of the bit from the fitting by use of an invented hand tool.

FIG. 6 illustrates removal of harvested bone material from the bit by use of an invented hand tool.

DETAILED DESCRIPTION OF THE PREFERRED EMBODIMENT

Distal and proximal, as used herein, are from the perspective of the drill or drilling machine to which the invented drill bit and fitting are fitted in use. Thus, proximal means relatively inwardly or nearer the drill's chuck and distal means relatively outwardly or farther therefrom. Generally, then, it will be appreciated that the invented drill bit's distal end performs the harvesting work on the bone and its proximal end is affixed to the distal end of the fitting, the proximal end of which is affixed to the distal end of the drill's chuck.

Referring collectively to FIGS. 1 through 4, the invented drill bit, slightly enlarged in FIG. 1 and greatly enlarged in FIGS. 1 through 4, is generally indicated at 10, with a drill chuck 11 illustrated schematically in phantom (dashed) outline in FIG. 1. Drill bit 10 preferably is formed with an elongate, cylindrical, hollow shank 12 having a proximal end with one or more, and preferably two, elongate slotted recesses formed therein for receiving therein a securing post of a drill head or chuck-and-fitting combination; and having on its distal end a semicircumferentially extending conical expanse defining a cutter, or cutting head or tip generally indicated at 14. As shown in FIG. 1, cutting tip 14 is provided with a first, sharpened, lip or edge 16 which joins in a sharp point 18 at the conical expanse's apex with another, non-sharpened lip or edge 20. Sharpened edge 16 is configured to cut into bone, as shown in FIG. 2. More specifically, as shown in FIG. 2, when drill bit 10 is rotated in a clockwise direction (indicated by the arcuate arrow in FIG. 2), with point 18 directed against a section of bone 22, cutting edge 16 shears off fragments of bone 22 and deflects the fragments 22' through hollow shaft 12 toward its proximal end. As drill bit 10 is forced deeper inwardly of the donor bone, continuous cutting action occurs and a desired accumulation of morselized bone can then be removed from the shaft and used to build up bone in other areas to which it is transplanted.

Briefly describing the preferred manufacture of bit 10, those of skill in the art will appreciate that preferably it is machined out of stainless steel bar stock. After turning the piece and boring a distally extending central, axial bore therein, the cutting tip opening is formed, also by machining or by hand. When the drill bit has its basic shape, it is glass bead blasted to provide a bur-free, smooth finish. Drill bit 10 then is rendered corrosion-resistant by hardening it to approximately 38–42 Rockwell. Preferably such hardening is performed by heating the bit to approximately 875° F. for approximately one hour. Finally, the bit is resharpened to ensure that its cutting tip is capable. Persons of skill in the art will appreciate that alternative materials and processes may be used, within the spirit and scope of the invention.

It may be seen best from FIGS. 1 (edge view), 2 and 4, beveled (sharpened) cutting edge 16 preferably extends from apex 18 through a substantially straight region that extends all the way to the periphery of shank 12 and terminates adjacent a region of joinder between conical expanse 24 and cylindrical shank 12 in a rectilinear notch or opening visibly depicted in FIG. 1 at 14a. This notch, which may be seen to extend, or step, the cutting edge slightly proximally of the distal end of cylindrical shank 12, is believed to provide some chipping action as well as some directing action in terms of removing bone chips from the donor bone and collecting them in the hollow region of the shank. Notch 14a is an artifact of the manufacturing process by which the machined, smoothed and hardened stainless steel bit is re-machined either automatically or by hand, as by the use of a dovetail file, to ensure the sharpness of cutting edge 16. (It is noted that trailing edge 20 has a smoothed arcuate feature (see FIG. 4) that also is an artifact of such final filing or machining step in the manufacture of invented drill bit. 10 but that has been rounded for aesthetic reasons.)

Preferably, conical expanse 14 in cross section may be seen to extend distally and inwardly (or toward the central long axis of the drill bit) at a predefined angle relative the long axis of shank 12. It may be seen from FIG. 3 that the angle between the distally, inwardly extending conical expanse 24 (and, most importantly, the inner surface thereof) relative to the long axis of shank 12 preferably is between approximately 40° and 80°, more preferably is between approximately 45° and 75°, even more preferably is between approximately 50° and 70° and most preferably is approximately 60°. These angles are designated θ in FIG. 3, which preferably identical angles θ represent the angles between any straight line such as lines $C^1$, $C^2$ extending along the conical expanse and intersecting at its apex, and the long axis A of shank 12. It will be understood that the sum of angles θ represents an obtuse, and preferably approximately 120° angle between opposite edges of conical expanse 24 represented by lines $C^1$, $C^2$. This produces an unexpected advantage of invented drill bit 10 over conventional drilling tools. It is believed that the relatively broad angle provides the needed deflection of chipped bone particulate generally in parallel with long axis A of shank 12, thereby ensuring its accumulation therewithin and thereby reducing or eliminating waste in the bone-harvesting process.

Referring briefly to FIG. 4, which is an end view of drill bit 10 in its preferred embodiment, it may be seen that conical expanse 24 extends partly circumferentially, or semicircumferentially. Preferably, this semicircumferential expanse extends through an arc that is between approximately 120° and 240°, more preferably it extends through an arc that is between approximately 150° and 210° and most preferably it extends through an approximately 180° arc. This arcuate extent of the semicircumferential expanse is designated Φ in FIG. 4, which angle Φ represents the angle between a line $D^1$ marking leading or cutting edge 16 of conical expanse 24 of drill bit 10 and a line $D_2$ marking trailing or non-cutting edge 20 thereof. It is believed that this arcuate angle through which conical expanse 24 extends represents an important tradeoff between the effective cutting capability and the effective collecting capability of the drill bit. With a lesser arcuate extent, the conical expanse might lack durability and might provide too little surface area for deflection of bone chips into shank 12. With a greater extent, the conical expanse might produce too much frictional resistance to rotation and might complicate removal of harvested bone material from shank 12, a preferred means for which will be described by reference to FIG. 6.

It is noted by reference to FIG. 1 that there preferably is provided one or more, and more preferably there is provided a series of axially spaced, parallel, circular scores such as scores 26a, 26b, 26c formed in the outer surface of shank 12. The purpose of such scores is to provide a calibrated measure of the amount of material that is needed, thereby to indicate to the person harvesting the bone when sufficient material has been collected. Scores 26a, 26b, 26c are calibrated preferably to indicate a linear depth measure from the outer extreme of cylindrical shank 12 (not counting the extent of the conical section cutting tip therebeyond), but it will be appreciated that they alternatively or additionally may indicate any useful measure such as material volume. The scores, or score lines, that are shown best in FIG. 3 indicate 10 mm (1 cm), 20 mm (2 cm) and 30 mm (3 cm) depths, and are interpretable by the user as indicating generally the depth of the drill bit's penetration into the donor bone. The lines will be understood to indicate to a substantial degree the amount of material within shank 12 after drilling, since very little material is lost and it is effectively packed during collection within shaft 12 so that its density does not change appreciably.

It may be seen from FIGS. 1 and 3 that a pair of elongate, diametrically opposed, oppositely inclined, slotted recesses 28a, 28b are formed in a proximal end region 12a of shank 12. Recesses 28a, 28b will be understood to matingly engage a crossbar member 30 fixed within a cylindrical bore 32a of a fitting 32 to provide locking rotational engagement therebetween when the drill is operated. In its preferred embodiment, each of recesses 28a, 28b preferably includes a region extending distally spirally from the proximal end region 12a of shank 12, as best seen in FIGS. 1 and 3. Referring to FIG. 3, it may be seen that recess 28a (and likewise diametrically opposed recess 28b) preferably extends at an angle γ of between approximately 30° and 60° and more preferably at an angle of approximately 45° relative to the long axis of shank 12, which angle y is represented in FIG. 3 between axis B that parallels elongate recess 28a and long axis A of shank 12. It is believed that this angle γ represents an optimal tradeoff between a slot extending in a plane normal to long axis A, which perhaps would best capture drill bit 10 within fitting 32, and a slot extending parallel to long axis A, which would provide adequate engagement for rotation but which would provide no security against inadvertent separation.

FIGS. 1, 3 and 4 show that shank 12 of drill bit 10 is in its proximal end region 12a preferably has a larger diameter than a distal end region 12b thereof. This step-wise diametric dimensional change along the length of shank 12 provides for fitting of drill bit 10 to an adaptive fitting 32, yet permits its cutting head 14 to be suitably, and perhaps variably, sized for a specific bone-harvesting application. In accordance with the preferred embodiment of the invention, drill bit 10 is approximately 85 mm long overall and fitting 32 is approximately 45 mm long overall, although of course other dimensions are within the spirit and scope of the invention. Preferably, an array of bits is provided having nominal outside right-cylindrical diameters (ODs) of 8 millimeters (8 mm), 10 mm and 12 mm, thereby providing for a variety of bone penetration diameters corresponding thereto, and thereby simplifying calculations of desired penetration depth for a given bone material volume requirement. Those skilled in the art will appreciate that other diameters and lengths may be used, within the spirit and scope of the invention. Through one or more smoothed steps, proximal end region 12a at its greatest diameter preferably is approximately 16 mm and the overall outer diameter of fitting 32 preferably is approximately 22 mm, although of course other suitable dimensions may be used depending upon the application.

Fitting 32 may be manufactured of any suitable material and by any suitable process, such as that described above for drill bit 10, and may have any suitable proximal end configuration that renders it matable with existing drill chucks. It will also be appreciated that the securing post by which bit 10 is securably gripped may be rendered in the drill chuck itself, thereby obviating fitting 32. Nevertheless, it is an advantage of the invention that fitting 32 is adaptable to mate novel drill bit 10 with any one of several industry-available drill chucks.

Turning next to FIG. 5, it may be seen that a novel removal key 34 may be provided to facilitate removal of drill bit 10 from fitting 32. It may seen from FIG. 5 that proximal end region 12a of shank 12 of bit 10 is tightly captured within fitting 32. This tight capture or securement may be seen to be accomplished in accordance with invention in two ways: A split spring washer 36 is provided that is compressed around shank 12 and in interference fit within a circular detent 32aa formed within bore 32a of fitting 32; and a proximal region of the sidewall of each of two recesses 28a, 28b is in interference fit with crossbar member 30 within fitting 32. As is desirable to avoid inadvertent removal, bit 10 often is so securely fitted within fitting 32 that it cannot be easily removed by hand. For this reason removal key 34 is provided for insertion of its semicylindrical end region 34a into a diametrically opposed pair of circular holes 36a, 36b formed in the proximal region of shank 12. It will be appreciated that hole pair 36a, 36b is located precisely along shank 12 such that, with bit 10 fitted securely within fitting 32, semicylindrical end region 34a of key 34 snugly fits within a region of the semicylindrical extent of hole pair 36a, 36b that extends distally from the distal end of fitting 32.

To remove bit 10 from fitting 32, it is a simple matter, with semicylindrical end region 34a inserted as far as it will go into the emergent holes, to grasp the opposite end region 34b of key 34 (which end preferably extends at an angle transverse to the angle of end region 34a, as indicated in FIG. 5) and to twist or otherwise lever key 34 (as indicated by arcuate arrows) to impinge on the near or far edge of fitting 32, thus overcoming the spring's tension and the recesses' resistance by leveraging or prying bit 10 from fitting 32. FIG. 5 may be seen to best illustrate use of the key to remove the bit from the fitting immediately prior to such manual leveraging action by the user. FIG. 5 also will be understood to show the proximal end of fitting 32, which may assume any desired configuration for mating with a custom drill chuck or any of a variety of industry-standard drill chucks. It is appreciated that fitting 32 serves the purpose in accordance with invention of coupling the novel bone-harvesting drill bit with the industry standard, installed base of medical drilling machines.

Turning now to FIG. 6, a hand tool is indicated generally at 38 for removing harvested bone material 22' from shank 12 of drill bit 10. Removal tool 38 may be formed of a stiff cylindrical wire material, as shown. It may be formed at one end 38a into a loop that permits it to be digitally manipulated easily and perhaps hung on a peg. It may fixedly attach at another end a circular disk 38b of sufficiently small diameter and thickness to permit it to be introduced into an opening 14a of cutting end 14 of drill bit 10 and of sufficiently large diameter and thickness effectively to impinge upon, plunger- or piston-like, morselized bone material 22' to drive such bone material in a proximal direction out the proximal end region opening in drill bit 10. In this way, harvested bone material is readied for use in transplantation to a donee site.

Typically, the iliac crest of the hip bone is used as a bone donor region for harvested bone, which in its granulated or morselized form is best for transplanting because it can be packed into another area where bone has been eroded, for example in an arthritic joint or other area in which bone has been diminished. Thus, the invention may be understood also to take the form of a method of harvesting bone from a donor site.

Preferably, the method includes 1) providing a bit 10 including a proximal hollow shank 12 and a distal cutter 14 including an opening to hollow shank 12, such opening being defined by a semicircumferentially extending conical expanse 24 having a point 18 at an apex thereof; 2) positioning bit 10 with such point 18 at a donor site of a bone 22; 3) rotating bit 10 at a defined speed, e.g. preferably approximately 200 revolutions per minute (RPM), with such cutter producing bone chips 22' and with such conical expanse 24 directing such produced bone chips 22' proximally through such opening into hollow shank 12; and 4) collecting such directed bone chips 22' in hollow shank 12 to produce a harvest of bone chips 22' therein for subsequent use.

Preferably, the method further includes providing fitting 32 for securely capturing a proximal terminal end of bit 10 therein and for fitting captured bit 10 to a drill for performing the rotating step. Also preferably, the method further includes providing a hand tool such as removal key 34 for what will be referred to herein as snap-removing bit 10 from its secure capture within fitting 32, as is described and illustrated herein with reference to FIG. 5. Preferably, the method further includes providing a hand tool 38 for urging harvested bone chips 22' proximally within hollow shank 12 and out of an opening formed in an extreme proximal end of bit 10 for such use, as is described and illustrated herein with reference to FIG. 6.

Preferably, the invented method further includes, preferably prior to such positioning step, inserting bit 10 into fitting 32 by urging the bit axially therealong. This inserting step, due to the novel structure and cooperation of recesses 28a, 28b and crossbar member 30, results in relative rotation between bit 10 and fitting 32, with the rotation being effected by providing on either bit 10 or fitting 32 a cam such as crossbar member 30 of fitting 32 and by providing on the other of bit 10 and fitting 32 a follower such as diametrically opposed, oppositely inclined elongate recesses 28a, 28b in proximal end 12a of shank 12. The cam and follower will be understood by those of skill in the art to cooperate to provide such rotation incident to the inserting step. Those of skill will appreciate that alternative camming configurations are possible, and are within the spirit and scope of the invention.

The invented apparatus may be seen to represent a significant improvement in a drill bit used in connection with bone grafting, the drill bit having a distal cutting tip and a proximal shank for rotation by a drill chuck. The improvement might be characterized as including a hollow collector region 40 (see FIG. 2) formed within the drill bit's shank 12 for receiving and collecting bone chips 22' therein, and an opening 42 (see FIG. 2) to collector region 40, opening 42 being formed adjacent cutting tip 14. In accordance with invention, cutting tip 14 is configured to produce bone chips such as bone chips 22' during rotation of drill bit 10 by the drill chuck and to deflect such produced bone chips 22' proximally into collector region 40. Such an improvement is perhaps best illustrated in FIG. 2.

As indicated above, cutting tip 14 preferably includes a semicircumferential conical expanse 24 terminating in a point 18 at the apex thereof, wherein the angle θ between a line $C^1$ or $C^2$ that extends along the expanse and that intersects at the apex and long axis A of shank 12 preferably is between approximately 40° and 80°, more preferably is between approximately 50° and 70° and most preferably is approximately 60°. As described and illustrated herein, hollow collecting region 40 extends through to the proximal terminal end of shank 12, thereby providing a convenient means for removal of collected bone chips 22', as, for example, by the use of plunger-like hand tool 38.

Preferably, improved drill bit 10 is for use with a fitting 32 having a securing post such as crossbar member 30 within a bore 32a therein for receiving drill bit 10, wherein shank 12 has formed in the proximal terminal end thereof one or more, and preferably two, elongate slotted recesses 28a, 28b formed therein for receiving the securing post therein, wherein each of recesses 28a, 28b includes a region extending distally spirally from the shank's proximal terminal end, as perhaps best illustrated in FIGS. 1 and 3, and as described in detail above. In brief summary, the invented drill bit and the method for its use in harvesting bone provides not only for producing bone chip material for grafting purposes, but conveniently also provides for collecting such bone chip material within the drill bit's hollow shaft. The invented drill bit and fitting conveniently and securely snap-fit together and may be easily snap-removed from one another and the harvested bone material removed from the bit's collecting region by the use, for example, of the invented hand tools.

While the present invention has been shown and described with reference to the foregoing preferred method and embodiment, it will be apparent to those skilled in the art that other changes in form and detail may be made therein without departing from the spirit and scope of the invention as defined in the appended claims.

We claim:

1. A bone-harvesting drill bit comprising:
   an elongate generally cylindrical hollow shank section having a distal end and a proximal end and a long axis extending therebetween, the distal end having first and second points disposed on the perimeter thereof; and
   a tip section extending from the distal end of the hollow shank, the tip section defined by a first lip extending from the first point on the distal end of the hollow shank to an apex located on the long axis, a second lip extending from the second point to the apex and a solid portion extending between said lips from said hollow shank to a sharp point at the apex, where the solid portion has an interior surface and an exterior surface and the first lip has a bevel between the interior and exterior surfaces to form an acutely sharp cutting edge at the exterior surface so that the drill bit may be rotated so that the cutting edge cuts the bone and the bevel guides resulting bone chips into the hollow shank.

2. The bit of claim 1, wherein said lips intersect the long axis at the apex at an angle of between approximately 40° and 80°, where said angle is measured between each lip and the long axis.

3. The bit of claim 2, wherein said angle is between approximately 50° and 70°.

4. The bit of claim 2, wherein said angle is approximately 60°.

5. The bit of claim 1, wherein said cutting edge extends from the apex through a substantially straight region to said first point.

6. The bit of claim 1 for use with a drill head having distal spindle with a securing post and wherein said proximal end of said shank includes an elongate slotted recess for receiving the securing post.

7. The bit of claim 6, wherein said recess includes a region extending distally spirally from said shank's proximal end.

8. The bit of claim 1, wherein said solid section extends through an arc between said first and second points having an arc length between approximately 120° and 240°.

9. The bit of claim 8, wherein the arc length is between approximately 150° and 210°.

10. The bit of claim 9, wherein the arc length is approximately 180°.

11. The bit of claim 1, wherein the exterior surface of said solid section is shaped substantially like a semicircumferentially extending cone.

12. The bit of claim 11 wherein said first lip follows a substantially straight path between the first point and the apex.

13. The bit of claim 11 wherein said second lip follows a substantially straight path between the second point and the apex.

14. A method for harvesting bone from a donor site, the method comprising the steps of:
   providing a bit including an elongate generally cylindrical hollow shank section having a distal end and a proximal end and a long axis extending therebetween, the distal end having first and second points disposed on the perimeter thereof, and a tip section extending from the distal end of the hollow shank, the tip section defined by a first lip extending from the first point on the distal end of the hollow shank to an apex located on the long axis, a second lip extending from the second point to the apex and a solid portion extending between said tips from said hollow shank to a sharp point at the apex between said lips, where the solid portion has an interior surface and an exterior surface and the first lip has a bevel between the interior and exterior surfaces to form an acutely sharp cutting edge at the exterior surface;

positioning such bit with such sharp point at the donor site of a bone;

rotating such bit at a defined speed with such sharp cutting edge producing bone chips and with such bevel directing such produced bone chips proximally through such opening into such hollow shank; and collecting such directed bone chips in such hollow shank to produce a harvest of bone chips therein for subsequent use.

15. The method of claim 14 which further comprises providing a fitting for securely capturing a proximal terminal end of such bit therein and for fitting such captured bit to a drill for performing said rotating step.

16. The method of claim 15 which further comprises providing a hand tool for snap-removing such bit from its secure capture within such fitting.

17. The method of claim 16 which further comprises providing a hand tool for urging harvested bone chips proximally within such hollow shank and out of an opening formed in an extreme proximal end of such bit for such use.

18. The method of claim 15 which further comprises inserting such bit into such fitting by urging such bit axially therealong.

19. The method of claim 18, wherein said inserting results in relative rotation between such bit and such fitting, with said rotation being effected by providing on one of such bit and such fitting a cam and by providing on the other of such bit and such fitting a follower, whereby such cam and such follower cooperate to provide such rotation incident to said inserting.

* * * * *